(12) United States Patent
Freedman et al.

(10) Patent No.: US 6,765,380 B2
(45) Date of Patent: Jul. 20, 2004

(54) DETERMINING WETTABILITY OF AN OIL RESERVOIR USING BOREHOLE NMR MEASUREMENTS

(75) Inventors: Robert Freedman, Houston, TX (US); Martin D. Hurlimann, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 149 days.

(21) Appl. No.: 10/064,651

(22) Filed: Aug. 2, 2002

(65) Prior Publication Data

US 2004/0000905 A1 Jan. 1, 2004

Related U.S. Application Data

(60) Provisional application No. 60/382,786, filed on May 23, 2002.

(51) Int. Cl.[7] ................................................. G01V 3/00
(52) U.S. Cl. ........................................ 324/303; 324/300
(58) Field of Search ................................. 324/303, 300, 324/307, 312, 338; 73/155

(56) References Cited

U.S. PATENT DOCUMENTS

| | | | | |
|---|---|---|---|---|
| 3,597,681 | A | 8/1971 | Huckabey | 324/303 |
| 4,717,878 | A | 1/1988 | Taicher et al. | 324/303 |
| 4,860,581 | A | 8/1989 | Zimmerman et al. | 324/303 |
| 4,936,139 | A | 6/1990 | Zimmerman et al. | 324/303 |
| 5,055,787 | A | 10/1991 | Kleinberg et al. | 324/303 |
| 5,055,788 | A | 10/1991 | Kleinberg et al. | 324/303 |
| 5,280,243 | A | 1/1994 | Miller | 324/303 |
| 5,629,623 | A | 5/1997 | Sezginer et al. | 324/303 |
| 5,757,186 | A | 5/1998 | Taicher et al. | 324/303 |
| 5,914,598 | A | 6/1999 | Sezginer et al. | 324/303 |
| 6,111,409 | A | 8/2000 | Edwards et al. | 324/303 |
| 6,229,308 | B1 | * 5/2001 | Freedman | 324/303 |
| 6,232,778 | B1 | 5/2001 | Speier et al. | 324/303 |
| 6,237,404 | B1 | 5/2001 | Crary et al. | 324/303 |
| 6,246,236 | B1 | 6/2001 | Poitzsch et al. | 324/303 |
| 6,255,817 | B1 | 7/2001 | Poitzsch et al. | 324/303 |
| 6,291,995 | B1 | 9/2001 | Speier et al. | 324/303 |
| 6,297,632 | B1 | 10/2001 | Speier | 324/303 |

(List continued on next page.)

FOREIGN PATENT DOCUMENTS

WO    WO 01/42817 A1    6/2001

OTHER PUBLICATIONS

R. Freedman et al., "Wettability, Saturation, and Viscosity using the Magnetic Resonance Fluid Characterization Method and New Diffusion–Editing Pulse Sequence," *SPE 77397*, 2002 SPE Annual Technical Conference and Exh., San Antonio, Tx Sep. 29–Oct. 2, 2002 (pp. 1–13).

(List continued on next page.)

*Primary Examiner*—Edward Lefkowitz
*Assistant Examiner*—Brij Shrivastav
(74) *Attorney, Agent, or Firm*—Kevin P. McEnaney; Brigitte I. Jefferey; John J. Ryberg (57) ABSTRACT

A method for determining downhole reservoir wettability includes acquiring a first set of NMR measurements of formation fluids in earth formations at a selected axial depth; inverting the first set of the NMR measurements to produce a first distribution of a spin relaxation parameter for a fluid component in the formation fluids; acquiring a second set of NMR measurements of a formation fluid sample removed by a formation fluid testing tool at the selected axial depth, the formation fluid sample being kept at a substantially same pressure and temperature as those of the formation fluids in the earth formations at the selected axial depth; inverting the second set of NMR measurements to produce a second distribution of the spin relaxation parameter for the fluid component in the formation fluid sample; determining the reservoir wettability from a comparison of the first and second distributions of the spin relaxation parameter.

14 Claims, 6 Drawing Sheets

U.S. PATENT DOCUMENTS

| | | |
|---|---|---|
| 6,326,784 B1 | 12/2001 | Ganesan et al. ............ 324/303 |
| 6,346,813 B1 | 2/2002 | Kleinberg .................. 324/303 |
| 6,366,089 B1 | 4/2002 | Poitzsch et al. ............ 324/303 |
| 6,373,248 B1 | 4/2002 | Poitzsch et al. ............ 324/303 |
| 6,392,410 B2 | 5/2002 | Luong et al. ............... 324/303 |
| 6,400,147 B1 | 6/2002 | Toufaily et al. ............ 324/303 |
| 6,492,809 B1 | 12/2002 | Speier et al. ............... 324/303 |
| 6,518,757 B1 | 2/2003 | Speier ........................ 324/303 |
| 6,518,758 B1 | 2/2003 | Speier et al. ............... 324/303 |
| 6,528,995 B1 | 3/2003 | Speier et al. ............... 324/303 |
| 6,531,869 B1 | 3/2003 | Speier et al. ............... 324/303 |
| 6,538,438 B1 | 3/2003 | Speier et al. ............... 324/303 |
| 6,566,874 B1 | 5/2003 | Speier et al. ............... 324/303 |
| 6,570,381 B1 | 5/2003 | Speier et al. ............... 324/303 |

OTHER PUBLICATIONS

RJS Brown & I Fatt, "Measurements of Fractional Wettability of Oilfield Rocks by the Nuclear magnetic Relaxation Method," *Petroleum Transactions AIME*, pp. 262–264, Petroleum Branch Fall Meeting, Los Angeles, Cal. (Oct. 14–17, 1956).

FF Craig, Jr., "Basic Water–Oil Flow Properties of Reservoir Rock," *The Reservoir Engineering Aspects of Waterflooding*, Ch. 2, pp. 12–28, Soc'y of Petroleum Engineers of AIME (1971).

NR Morrow, "Wettability and Its Effect on Oil Recovery," *SPE J. Petroleum Technology*, pp. 1476–1484 (Dec. 1990).

GQ Zhang, C–C Huang & GJ Hirasaki, "Interpretation of Wettability in Sandstones with NMR Analysis," *Petrophysics*, vol. 41, No. 3, pp. 223–233 (May–Jun. 2000), originally presented Int'l Symposium Soc'y Core Analysts, Golden Colo. (Aug. 1–4, 1999).

R Freedman, S Lo, M Flaum, GJ Hirasaki, A Matteson & A Sezginer, A New NMR Method of Fluid Characterization in Reservoir Rocks: Experimental Confirmation and Stimulation Results, *SPE Journal*, pp. 452–464 (Dec. 2001), originally presented SPE 63214 SPE Ann. Tech. Conf. & Exh., Dallas Tex. (Oct. 1–4, 2000).

MD Hurlimann, "Diffusion and Relaxation Effects in General Stray Field NMR Experiments," *J. Magnetic Resonance* 148, pp. 367–378 (2001).

R Freedman, N Heaton & M Flaum, "Field Applications of a New Nuclear Magnetic Resonance Fluid Characterization Method," *SPE 71713*, pp. 1–12, SPE Ann. Tech. Conf. & Exh., New Orleans, La. (Sep. 30–Oct. 3, 2001).

MD Hurlimann, L Venkataramanan, C Flaum, P Speier, C Karmonik, R Freedman & N Heaton, "Diffusion–Editing: New NMR Measurement of Saturation and Pore Geometry," *SPWLA*, pp. 1–14, $43^{rd}$ Ann. Logging Sym., (Jun. 2–5, 2002).

* cited by examiner

DETERMINING WETTABILITY OF AN OIL RESERVOIR USING BOREHOLE NMR MEASUREMENTS

CROSS REFERENCE TO RELATED APPLICATIONS

This invention claims priority of U.S. Provisional Application Serial No. 60/382,786, filed on May 23, 2002, by Freedman and Hürlimann, entitled "Determining Wettability of an Oil Reservoir Using Borehole NMR Measurements."

BACKGROUND OF INVENTION

1. Field of the Invention

The present invention relates to the field of well logging. More specifically, the present invention relates to methods for determining wettability of oil reservoir using nuclear magnetic resonance data.

2. Background Art

Wettability is the tendency of a fluid to spread on and preferentially adhere to or "wet" a solid surface in the presence of other immiscible fluids. Knowledge of the wettability of an oil reservoir is important to reservoir and production engineers because reservoir wettability influences reservoir properties such as residual oil saturation, relative permeability, and capillary pressure. See F. G. Craig in the Society of Professional Engineers (SPE) Monograph on "The Reservoir Engineering Aspects of Waterflooding", 1971. Thus, reservoir wettability information is crucial for efficient oil recovery. This information is becoming increasingly important as secondary and tertiary recovery methods are used to recover remaining reserves in old producing fields. For example, in a water-wet reservoir, a waterflood can be an efficient method of recovering remaining reserves after primary production, whereas, in a mixed-wet reservoir, a surfactant flood would be more effective in recovering the remaining oil.

Two widely-used wettability indicators are contact angles in water-oil-solid systems and the Amott wettability index. In addition, other laboratory tests for wettability are also available, including imbibition measurements. However, these are laboratory measurements and cannot be performed downhole. In contrast, a nuclear magnetic resonance (NMR) approach can provide a qualitative wettability indicator and has the advantage of being able to assess the fluids and rock at reservoir conditions.

NMR measurements on fluid saturated rocks are sensitive to the wettability of the rock matrix because relaxation rates of fluid molecules are enhanced when they are in contact with rock surfaces. This is because rock surfaces often have paramagnetic ions or magnetic ions which can provide efficient relaxation for the fluid molecules. Reservoir wettability not only depends on the inherent property of the rock matrix, but also on surface interactions between the rock matrix and the fluid molecules, i.e., it also depends on the attractive Coulomb forces that exist between the polar oil molecules and those on rock matrix surfaces.

Many laboratory NMR wettability studies have been reported in the literature. The first NMR study on wettability was by Brown and Fatt, who made $T_1$ relaxation measurements on water-saturated unconsolidated sand packs constructed with different fractions of water-wet and oil-wet sand grains. See R. J. S. Brown and I. Fatt, "*Measurements of Fractional Wettability of Oilfield Rocks by the Nuclear Magnetic Relaxation Method*," Petroleum Transactions, AIME, 207, pp. 262–264, 1956. Numerous studies on the application of NMR to wettability have been published since then. See Q. Zhang, C. C. Huang, and G. J. Hirasaki, "*Interpretation of Wettability in Sandstones with NMR Analysis*," Petrophysics, May–June, 2000, vol. 41, No. 3, pp. 223–233.

Prior NMR studies of wettability of partially saturated reservoir rocks have been mostly limited to rocks saturated with brine and low viscosity hydrocarbons, such as Soltrol, decane, and dodecane. These low viscosity fluids ae characterized as having narrow $T_1$ and $T_2$ distributions and long relaxation times. Accordingly, it is relatively simple to distinguish the hydrocarbon signal from the brine signal in the relaxation time distributions of partially saturated rocks. The oil relaxation times in the rocks can then be compared with those of the bulk hydrocarbon (i.e., outside the rock) to infer whether the oil is wetting the surface. However, wettability inferred from experiments using refined or pure hydrocarbons is not indicative of the wettability of the same rocks saturated with crude oil, because crude oils may contain asphaltenes and resins, which are known to have surface-active polar molecules that are attracted to opposite charge sites on the pore surfaces.

The above described approaches to the determination of rock wettability use laboratory measurements. Reservoir wettability determination from laboratory measurements is not definitive because it is not possible to accurately mimic reservoir conditions in the laboratory. In fact, the very processes required to obtain laboratory samples can alter the reservoir wettability. See N. R. Morrow, "*Wettability and Its Effect on Oil Recovery*" in the J. of Pet. Tech., December, 1990, pp. 1476 1484. Therefore, it is desirable to have methods that can determine reservoir wettability under downhole conditions.

SUMMARY OF INVENTION

One aspect of the invention relates to methods for determining reservoir wettability under downhole conditions. A method for determining downhole reservoir wettability according to the invention includes acquiring a first set of NMR measurements of formation fluids in earth formations at a selected axial depth; inverting the first set of the NMR measurements to produce a first distribution of a spin relaxation parameter for a fluid component in the formation fluids; acquiring a second set of NMR measurements of a formation fluid sample removed by a formation fluid testing tool at the selected axial depth, the formation fluid sample being kept at a substantially same pressure and temperature as those of the formation fluids in the earth formations at the selected axial depth; inverting the second set of NMR measurements to produce a second distribution of the spin relaxation parameter for the fluid component in the formation fluid sample; determining the reservoir wettability from a comparison of the first and second distributions of the spin relaxation parameter.

Other aspects of the invention would become apparent from the following description, the drawings, and the claims.

DETAILED DESCRIPTION

Embodiments of the invention relate to methods for determining reservoir rock wettability under downhole conditions. Methods according to the invention involve two suites of NMR measurements: one suite is obtained with formation fluids in the reservoir rocks in earth formations, and the other suite is obtained with formation fluids removed from the reservoir rock, for example, using a fluid testing tool. It is preferred that the removed fluid sample be maintained at substantially the same conditions (e.g., same pressure and temperature) as it was in earth formations. The first suite of measurements may be performed with any NMR logging tool, whether a wireline tool or a measurement-while-drilling (MWD) tool, while the second suite of measurements may be performed with any formation fluid testing tool with an NMR module or with a laboratory NMR instrument using a formation fluid sample removed with a conventional formation fluid testing tool. Examples of wireline NMR logging tools include U.S. Pat. No. 4,717,878 issued to Taicher et al. and U.S. Pat. No. 5,055,787 issued to Kleinberg et al. Example of MWD NMR tools include U.S. Pat. No. 5,280,243 issued to Miller and U.S. Pat. No. 5,757,186 issued to Taicher et al. For formation fluid sampling, various formation fluid testing tools are known in the art. For example, U.S. Pat. Nos. 4,860,581 and 4,936,139 both issued to Zimmerman et al. disclose downhole tools that extract samples for determining formation properties such as permeability and pressure profile. More recently, NMR instruments have been incorporated in formation fluid testing tools for analyzing properties of hydrocarbons downhole. For example, U.S. Pat. No. 6,111,409 issued to Edwards et al. and U.S. Pat. No. 6,346,813 B1 issued to Kleinberg disclose formation fluid testing tools that include NMR modules for analysis of connate fluids removed from the formations.

Figures 1, 2:
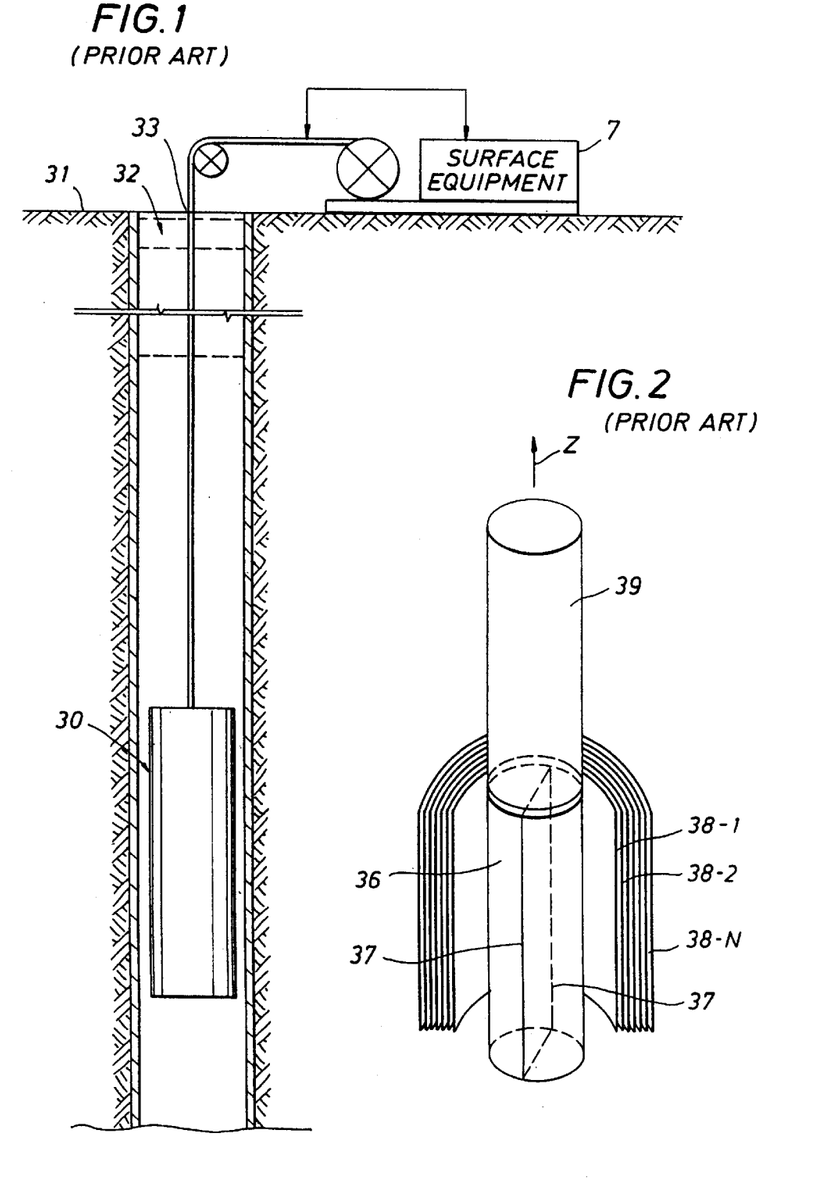
FIG. 1 is a diagram of a nuclear magnetic resonance tool in a borehole penetrating earth formations.
FIG. 2 is a diagram illustrating components of a nuclear magnetic resonance tool.

FIG. 1 shows a nuclear magnetic resonance (NMR) logging tool 30 for investigating earth formations 31 traversed by a borehole 32. The NMR logging device 30 is suspended in the borehole 32 on an armored cable 33, the length of which substantially determines the relative axial depth of the device 30. The cable length is controlled by suitable means at the surface such as a drum and winch mechanism (not shown). Surface equipment 7 can be of conventional type and can include a processor subsystem which communicates with downhole equipment including NMR logging device 30.

The NMR logging device 30 can be any suitable nuclear magnetic resonance logging device; it may be one for use in wireline logging applications as shown in FIG. 1, or one that can be used in measurement-while-drilling (MWD) applications. The NMR logging device 30 typically includes a means for producing a static magnetic field in the formations, and a radio frequency (RF) antenna means for producing pulses of magnetic field in the formations and for receiving the spin echoes from the formations. The means for producing a static magnetic field may comprise a permanent magnet or magnet array, and the RF antenna means for producing pulses of magnetic field and receiving spin echoes from the formations may comprise one or more RF antennas.

A variety of NMR logging tools that may be used with methods of the present invention are known in the art. FIG. 2 illustrates a schematic of some of the components of one type of NMR logging device 30. FIG. 2 shows a first centralized magnet or magnet array 36 and an RF antenna 37, which may be a suitably oriented coil or coils. FIG. 2 also illustrates a general representation of closely-spaced cylindrical thin shells, 38-1, 38-2 . . . 38-N, that can be frequency selected in a multi-frequency logging operation. One such device is disclosed in U.S. Pat. No. 4,710,713. In FIG. 2, another magnet or magnet array 39 is shown. Magnet array 39 may be used to pre-polarize the earth formation ahead of the investigation region as the logging device 30 is raised in the borehole in the direction of arrow Z. Examples of such devices are disclosed in U.S. Pat. Nos. 5,055,788 and 3,597,681.

Figure 3:
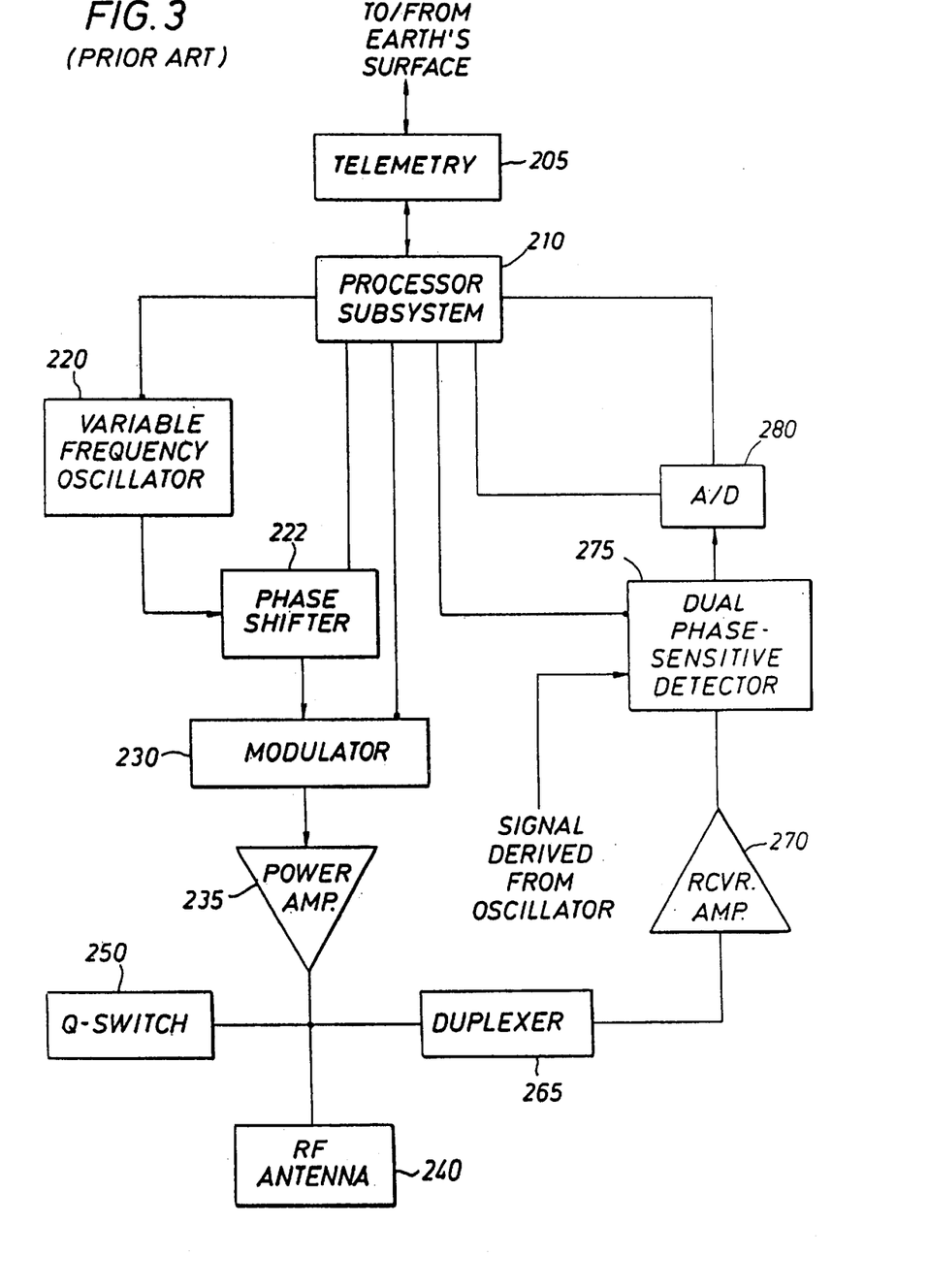
FIG. 3 illustrates a schematic diagram of a circuitry of an NMR tool for producing the RF pulses and for receiving and storing the spin echoes.

FIG. 3 illustrates a schematic of a circuitry of an NMR tool for producing the RF pulses and for receiving and storing the spin echoes. One skilled in the art would appreciate that any other suitable circuitry could be used without departing from the scope of the invention.

In FIG. 3, a downhole processor 210 has associated memory, timing, interfaces, and peripherals (not separately shown), as known in the art. The processor subsystem 210 is coupled with telemetry circuitry 205, for communication with a processor on the surface (not shown). The pulse forming circuitry includes a variable frequency oscillator 220 which, under control of processor 210, produces radio frequency (RF) signals at the desired frequencies. The output of oscillator 220 is coupled to a phase shifter 222 and then to a modulator 230, both of which are under the control of processor subsystem 210. The phase shifter 222 and modulator 230 can be controlled, in a manner known in the art, to produce the desired pulses of RF field, for example the 90 degree and 180 degree pulses for Carr-Purcell-Meiboom-Gill (CPMG) types of sequences or any other desired NMR pulse sequences. The output of modulator 230 is coupled, via a power amplifier 235, to the RF antenna 240. A Q-switch 250 can be provided to damp the RF antenna system to reduce antenna ringing. The antenna 240 is also coupled with a receiver section via duplexer 265, the output of which is coupled to receiver amplifier 270. The duplexer 265 protects the receiver amplifier 270 from the high power pulses which pass to the RF antenna 240 during the transmitting and damping modes. During the receiving mode, the duplexer 265 acts as a low impedance connection from antenna 240 to the receiver amplifier 270. The output of receiver amplifier 270 is coupled to a dual phase-sensitive detector 275, which also receives, as a reference, a signal derived from the oscillator signal. The detected output is coupled to analog-to-digital converter 280, the output of which is a digital version of the received nuclear magnetic resonance signal. Although the logging device or tool 30 is shown as a single body in FIG. 1, it may alternatively comprise separate components, and the tool may be combinable with other logging tools. Also, while a wireline is illustrated, alternative forms of physical support and communicating link can be used, such as those used in a measurement-while-drilling system.

Many tools known in the art are capable of withdrawing samples from the formations for analysis. These tools are generally referred to herein as "formation fluid testing tools." For example, U.S. Pat. Nos. 4,860,581 and 4,936,139 both issued to Zimmerman et al. disclose downhole tools that can extract samples for determining formation properties such as permeability and pressure profile. These patents were assigned to the same assignee as the present invention and are hereby incorporated by reference. These tools may have modules that can perform different analysis. Examples of such tools include Modular Formation Dynamics Testers sold under the trade name of MDT™ by Schlumberger Technology Corporation (Houston, Tex.). The modules on MDT™ may include an NMR instrument.

Figures 4, 6:
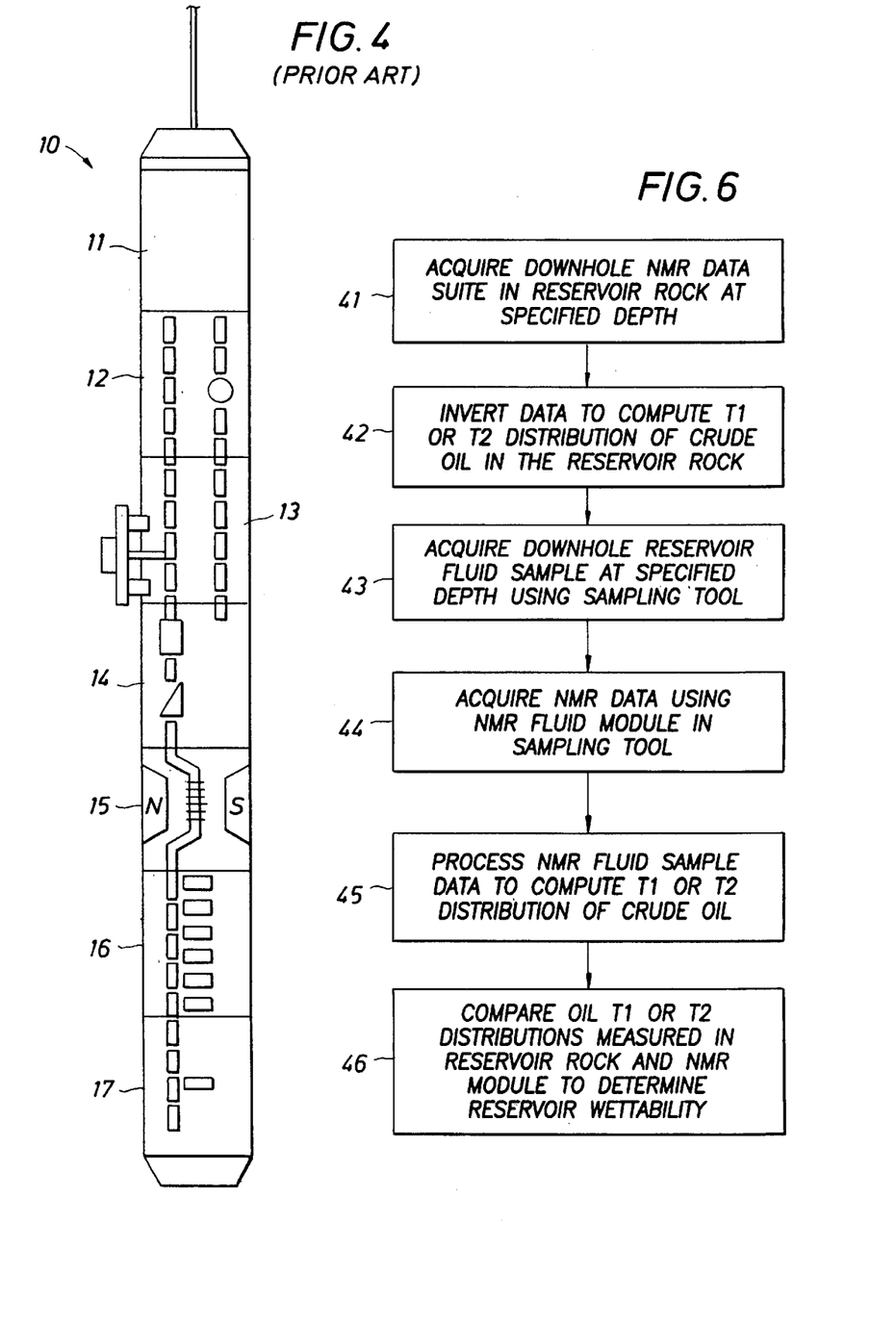
FIG. 4 is a diagram illustrating a formation fluid testing tool having an NMR module.
FIG. 6 shows a flow chart of a method according to one embodiment of the invention.

Modern formation fluid testing tools (e.g., MDT™ tool) are composed of several parts which enable extraction of fluids from permeable earth formations. FIG. 4 shows one example of a formation fluid testing tool 10 having several modules with different functions. The electric power module 11 and the hydraulic power module 12 power the tool. The probe module 13 is deployed so as to make a hydraulic seal with the formation. The seal makes it possible to withdraw connate fluids free from contaminations from the drilling mud. Tool 10 also has a pumpout module 17, which lowers the pressure in the flow line in a controlled manner so as to extract fluids from the formations while maintaining the pressure near the original formation pressure. Samples are optionally monitored by an optical fluid analyzer (OFA) 14 and/or other monitoring devices (not shown) that can monitor the properties (pressure, acidity, resistivity, etc.) of the withdrawn fluids. These monitoring devices are used to indicate when the fluids being withdrawn are free from contaminations by the drilling mud or mud filtrate and when the fluids can be retained for transportation to surface laboratories in the multisample module 16, or be analyzed by the analytical modules on the formation fluid testing tool.

The modular design of such tools permits other analysis and monitoring devices to be incorporated in these tools. For example, NMR module 15 may be included in the formation fluid testing tool 10. The NMR module, like a regular NMR well logging instrument, would include at least one permanent magnet (shown as N and S poles) for inducing static magnetic fields in the sample chamber and at least one antenna (not shown) for generating radio frequency magnetic field pulses and for receiving the NMR signal amplitudes. U.S. Pat. No. 6,346,813 B1 issued to Kleinberg discloses one such tool with an NMR module for NMR measurements. This patent is assigned to the same assignee as the present invention and is hereby incorporated by reference.

NMR measurements on fluid-saturated rock are sensitive to the wettability of the rock because relaxation rates of fluid molecules are enhanced when the fluid molecules contact pore surfaces on the rock that contains paramagnetic ions or magnetic impurities. Surface relaxation of nuclear magnetization is usually the dominant relaxation mechanism for the wetting phase in a partially saturated rock. The nonwetting phase is usually unaffected by surface relaxation because the pore surface is coated with the wetting fluid and the nonwetting phase is prevented from contacting the pore surface.

Thus, reservoir wettability may be determined by comparing NMR relaxation time (i.e., $T_1$ or $T_2$) distributions of a bulk crude oil sample with the relaxation time distributions of the same crude oil in the reservoir rock. For such a comparison to be meaningful, both measurements should be made at substantially the same temperature and pressure. If the center or the peak of the relaxation time distribution of the oil measured in the rock is shifted towards shorter relaxation times, as compared to the center or the peak of the relaxation time distribution of the bulk oil sample, then the rock/brine/oil system is mixed-wet or oil-wet. The shift towards shorter relaxation times results from enhanced surface relaxation of oil molecules that wet the pore surfaces. In the same mixed-wet or oil-wet rock, the relaxation time distribution of the brine or water phase in the rock, on the other hand, will be shifted towards longer relaxation times relative to that of a 100% brine-saturated rock. This is because water molecules in the oil-wet pores are prevented from contacting the pore surfaces, and, hence, they experience reduced or no surface relaxation.

Many mechanisms are responsible for relaxation of spin magnetizations, whether longitudinal or transverse relaxation. The following description uses the transverse relaxation to illustrate the principles of the invention. One skilled in the art would appreciate that similar analysis applies to longitudinal relaxation. The overall relaxation rate $$\left(\frac{1}{T_1^*}\right)$$

of a transverse magnetization measured in a spin-echo experiment is the sum of relaxation rates from three mechanisms, bulk relaxation, diffusion relaxation, and surface relaxation, i.e., $$\frac{1}{T_2^*} = \frac{1}{T_{2,bulk}} + \frac{1}{T_{2,diff}} + \frac{1}{T_{2,surf}}.$$

The bulk relaxation rates $$\left(\frac{1}{T_{1,bulk}}\right)$$

for liquids depends on their viscosities. The diffusion relaxation rates $$\left(\frac{1}{T_{1,diff}}\right)$$

depend on the diffusion contstants of the fluid molecules and the magnetic field gradient. The surface relaxation rates $$\left(\frac{1}{T_{1,surf}}\right)$$

are a function of surface relaxivity and the ratio of surface to effective volume of the fluid. Bulk and diffusion relaxations affect both the wetting and nonwetting phases, while surface relaxation affects only the wetting phase. Thus, surface relaxation can be sued to distinguish wetting from non-wetting phase.

The surface relaxation rate $$\left(\frac{1}{T_{1,surf}}\right)$$

of the wetting phase in a single pore can be written in the following form:

$$\frac{1}{T_{2,surf}} = \frac{\rho_2 S}{V_{eff}} \qquad (1)$$

where S is the surface area of the pore contacted by the fluid of interest and $\rho_2$ is the surface relaxivity, a parameter that accounts for the effectiveness of the surface in promoting spin-relaxation, and $V_{eff}$ is the volume occupied by the wetting phase fluid. $V_{eff}$ can be considerably less than the pore volume, especially at low wetting phase saturations. Therefore, in partially saturated rocks, surface relaxation does not depend simply on pore size and surface relaxivity, but also on fluid saturation. For example, in a mixed-wet reservoir at low or residual oil saturation the surface relaxation of the oil is enhanced, because of the reduced value of $V_{eff}$, as compared to the surface relaxation at higher oil saturations.

The above description illustrates that a fluid component that is a wetting phase will be subjected to surface relaxation. Accordingly, a fluid component that is a wetting phase will have a shorter $T_2$ value as compared to the same fluid in the absence of surface relaxation. This phenomenon suggests that a comparison of $T_2$ or $T_1$ distributions between the same fluids in the reservoir rocks and outside of the reservoir rocks should provide information as to whether a particular fluid component is the wetting phase. In order to do so, it is necessary that the $T_1$ or $T_2$ distributions be separable into individual fluid components. A magnetic resonance fluid characterization (MRF) method recently disclosed in U.S. Pat. No. 6,229,308 B1 issued to Freedman ("the Freedman patent") can provide $T_1$ or $T_2$ distributions for individual components in a mixture of fluids from a suite of NMR measurements. The Freedman patent is assigned to the same assignee as the present application and is hereby incorporated by reference. The method described in the Freedman patent will be referred to as the "magnetic resonance fluid characterization method" or the "MRF method."

The MRF method is a diffusion-based NMR fluid characterization method. The method uses the fact that decay of the transverse magnetization measured in a spin-echo experiment is due, in part, to molecular diffusion of the fluid molecules. Diffusion of molecules in an inhomogeneous static magnetic field causes the Larmor precession frequencies of the spins to become time dependent. This leads to imperfect refocusing of the spin-echo signals by the 180° pulses, and, therefore, to an irreversible diffusion-induced decay of the echoes. The diffusion decay rate of the transverse magnetization contributed by freely diffusing molecules that contain hydrogen nuclei is given by, $$\frac{1}{T_{2,diff}} = \frac{\gamma^2 g^2 t_e^2 D}{12} \qquad (2)$$

where $\gamma=2\pi\cdot 4258$ Hz/Gauss is the proton gyromagnetic ratio, g is the magnetic field gradient, $t_e$ is the inter-echo spacing, and D is the molecular diffusion coefficient.

The MRF fluid characterization method performs simultaneous inversions of suites of diffusion-encoded spin-echo data. The forward model used for the inversions is a multifluid relaxation model that in general includes contributions from all fluid components (e.g., brine, oil, and mud filtrate) that might be present in the rock pore spaces. Inversion using the MRF method can provide diffusion-free $T_2$ distributions for individual components.

The MRF method is capable of producing $T_1$ or $T_2$ distribution for each component in a mixture of fluids because the multifluid relaxation model incorporates a constituent viscosity model (CVM) that relates, on a molecular level, diffusion coefficient distributions (D) to relaxation time distributions ($T_1$ and $T_2$) in live and dead crude oils. See R. Freedman et al., "*A New NMR Method of Fluid Characterization in Reservoir Rocks: Experimental confirmation and Simulation Results,*" SPEJ, (December, 2001), pp. 452–464; and R. Freedman et al., "*Field Applications of a New Magnetic Resonance fluid Characterization Method,*" paper SPE 71713 presented at the 2001 SPE Annual Technical Conference and Exhibition, New Orleans, September 30–October 3. The correlation between distributions of relaxation times and molecular diffusion coefficients is used to constrain the inversion. The CVM was validated in experiments on hydrocarbon mixtures including live and dead crude oils. The constrained inversion leads to more robust and accurate computations of both brine and crude oil $T_2$ distributions in partially saturated rocks than would otherwise be possible.

To use the MRF method, the NMR data should include diffusion information. Diffusion information may be obtained using suites of CPMG measurements having different inter-echo spacings. For a detailed description of how to use the conventional CPMG sequences to encode diffusion information for MRF analysis, see the Freedman patent.

Alternatively, diffusion information in NMR data may be obtained with a new type of "diffusion-editing" ("DE") spin-echo sequence tailored for fluid typing. See M.D. Hürlimann et al., "*Diffusion-Editing: New NMR Measurement of Saturation and Pore Geometry,*" paper presented at the 2002 Annual Meeting of the Society of Professional Well Log Analysts, Osio, Japan, June 2–5; see also, WO 01/42817, entitled "*Simpler and More Robust Hydrocarbon Typing with Pulsed NMR.*" This application is assigned to the same assignee as the present invention and is hereby incorporated by reference. DE sequences (see FIG. 5) are similar to the CPMG sequences except that the initial two echoes are acquired with longer echo spacings and the third and subsequent echoes are acquired with shorter echo spacings. Diffusion information is encoded during the acquisition of the first two echoes, whereas the third and subsequent echoes provide bulk and surface relaxation time information at long acquisition times with little, if any, attenuation of the signal by diffusion. This pulse sequence is referred to herein as the "DE pulse sequence" or the "diffusion editing pulse sequence." Using a conventional CPMG sequence to encode the diffusion information requires a long inter-echo spacing, which results in poor bulk and surface relaxation time information because diffusion decay attenuates the signal after relatively few echoes. Consequently, a suite of data acquired with DE sequences provides diffusion information and better signal-to-noise ratio in the spin-echo data, as compared to an analogous suite acquired with CPMG sequences. DE sequences can provide more accurate and robust computations of brine and oil $T_2$ distributions in partially saturated rocks than CPMG sequences. However, while the DE sequences are preferred, it is within the scope of the present invention that other sequences, including the CPMG sequences, may be used. By accurately measuring crude oil $T_2$ distributions in a rock and comparing this $T_2$ distribution with that measured on the bulk fluid, one can infer the wettability of the rock.

Figure 5:
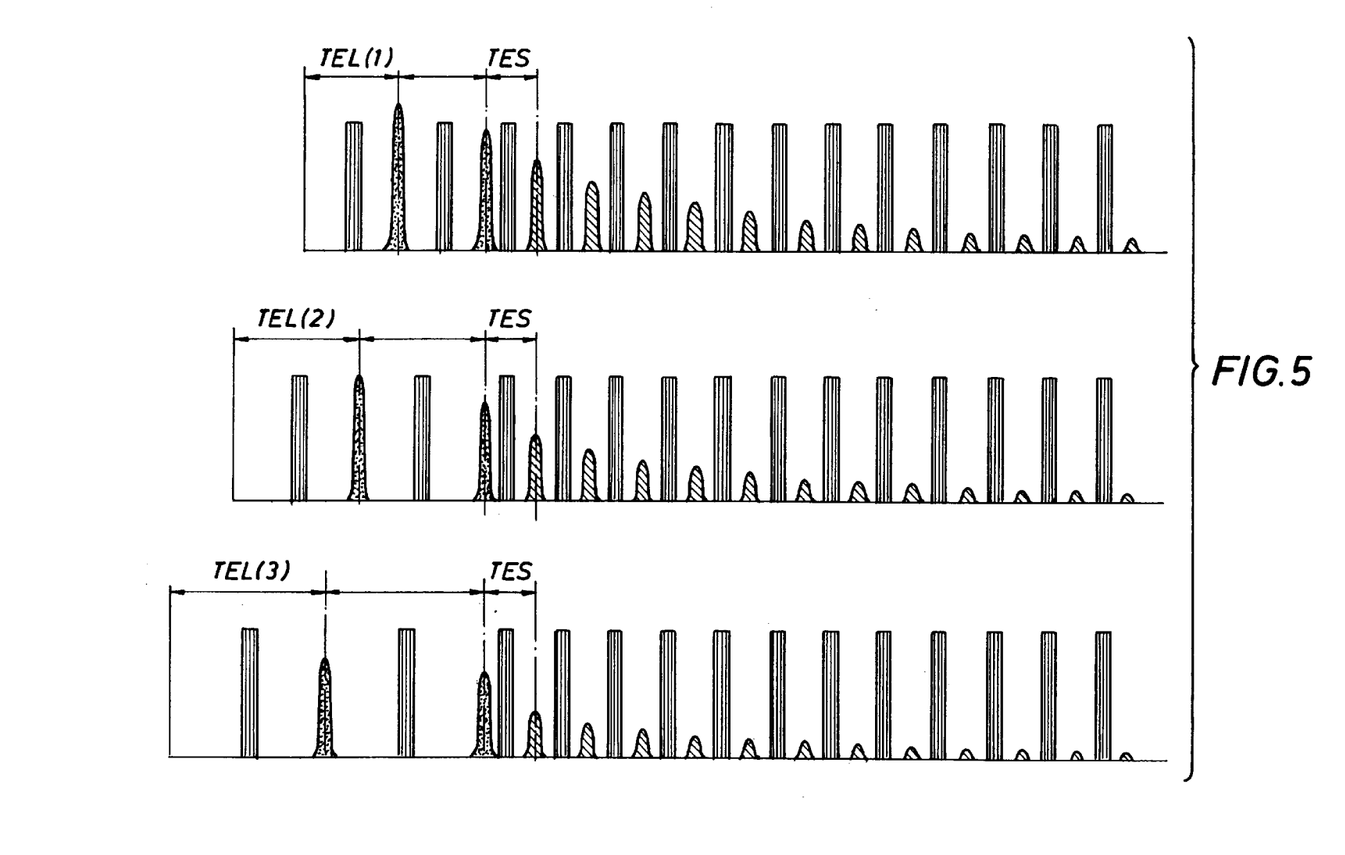
FIG. 5 shows three diffusion-editing pulse sequences with differing inter-echo delay times for the first two echoes.

FIG. 5 shows a suite of three fluid typing DE pulse sequences each having different initial long inter-echo spacings (TEL) for the first two echoes. The third and subsequent spin-echoes are acquired with the shorter inter-echo spacings (TES). While the DE pulse sequences are illustrated with only two initial long inter-echo spacings, one skilled in the art would appreciate that other numbers (e.g., 1, 3, 4, etc.) of long inter-echo spacings may be used without departing from the scope of the invention.

Once NMR data with diffusion information are obtained, they can be inverted with the MRF method to provide $T_2$ distributions for individual components in the fluids. The application of the MRF method to suites of NMR data obtained with conventional CPMG pulse sequences has been described in detailed in the Freedman patent. The following description will illustrate the application of the MRF multi-fluid relaxation model using NMR data obtained with DE pulse sequences.

For illustration, the following discussion uses a two-fluid model with brine and crude oil. One skilled in the art would appreciate that other fluid components (e.g., mud filtrate) may be added when necessary. The decay of the transverse magnetization, M(t), measured by a DE sequence for a two-fluid model can be written in the general form:

$$M(t, t_{e,l}) \approx \sum_{f=o,w} \int \int \int dD dT_1 dT_2 \qquad (3)$$

$$\left\{ P_f(D, T_1, T_2) \exp\left(-\frac{t}{T_2}\right) I(t, t_{e,l}, D) f(W, T_1) \right\}$$

The sum is over the two fluids, water and oil. $P_f(D, T_1, T_2)$ is a three-dimensional (3D) diffusion-relaxation time distribution function for each fluid. The function $f(W, T_1)$ corrects for insufficient recovery time (W) between DE sequences, e.g., $$f(W, T_1) = 1 - \exp\left(-\frac{W}{T_1}\right) \qquad (4)$$

The exponential $T_2$ decay factor in the integral includes surface relaxation for the wetting phase fluid and bulk relaxation for both fluids. The diffusion kernel, $I(t,t_{e,l}, D)$, for the third and subsequent echoes in the DE sequence was discussed by Hürlimann et al. in "*Diffusion-Editing: New NMR Measurement of Saturation and Pore Geometry*," presented at the 2002 Annual Meeting of the Society of Professional Well Log Analysts, Osio, Japan, June 2–5, and is given by $$I(t, t_{e,l}, D) = \qquad (5)$$

$$\left\{ a_d \exp\left(-\frac{\gamma^2 g^2 D t_{e,l}^3}{6}\right) + a_s \exp\left(-\frac{\gamma^2 g^2 D t_{e,l}^3}{3}\right) \right\} \times \exp\left(-\frac{\gamma^2 g^2 D t_{e,s}^2 t}{12}\right)$$

for $t > 2t_{e,l}$, where $t_{e,l}$ is the long echo spacing for the initial two echoes (see FIG. 5) and $t_{e,s}$ is the short echo spacing for the third and subsequent echoes in a DE sequence. The factor containing $t_{e,s}$ in Eq. 5 accounts for any diffusion-decay in an inhomogeneous magnetic field occurring during the acquisition of the third and subsequent echoes. Diffusion decay in an inhomogeneous magnetic field is biexponential, with the two contributions coming from direct and stimulated echoes. See Hürlimann, "*Diffusion and Relaxation Effects in General Stray Field NMR Experiments*," J. Magn. Reson. (2001), 148, 367–378. The direct and stimulated echo coefficients, $a_d$ and $a_s$, depend on the receiver bandwidth of the NMR instrument or logging tool. They can be determined by fitting the diffusion kernel in Eq. 5 to a suite of DE data acquired on a water sample. The diffusion kernel for the initial two echoes (e.g., for $t \leq 2t_{e,l}$) can be represented, to good approximation, by a single exponential decay factor, $$I(t, t_{e,l}, D) = \exp\left(-\frac{\gamma^2 g^2 D t_{e,l}^3 t}{12}\right). \qquad (6)$$

As with CPMG sequences, the first few echoes in a DE sequence are affected by off-resonance effects. These effects can be corrected by multiplying the first few echoes by spin-dynamics correction factors.

The 3D diffusion-relaxation time distribution function in Eq. 3, $P_f(D, T_1, T_2)$, may be extracted from inversion of the DE data suites. Alternatively, the MRF method may be used to extract this function. The MRF method takes advantage of the correlation between relaxation times and diffusion coefficients for fluids, e.g., water or crude oils. This simplifies the general forward model for the DE sequences in Eq. 3 because it reduces the 3D integral for each fluid to a simple one-dimensional (1D) integral over $T_2$. For example, the 3D diffusion-relaxation time distribution function for crude oils can be written in the form $$P_o(D,T_1,T_2) = P_o(T_2) \, \delta(D - \lambda T_2) \, \delta(T_1 - \xi_o T_2)$$

(7) where $P_o(T_2)$ is the diffusion-free $T_2$ distribution of the oil. The 1D distributions for D and $T_1$ are Dirac delta ($\delta$) functions. The parameter $\lambda$ in Eq. 7 relates the diffusion and relaxation time distributions in accordance with the CVM. For many dead crude oils, it has been established that an average value of $\lambda \approx 1.25 \times 10^{-5}$ cm$^2$/s$^2$ is appropriate. For live crude oils, $\lambda$ is multiplied by an empirically determined function of the solution gas/oil ratio, i.e., f(GOR). The average value of $\lambda$ given above is determined from the ratio of two empirically derived correlation parameters that relate the log means of diffusion and relaxation time distributions in crude oils to viscosity. Because of the approximate nature of empirical correlations, $\lambda$, for different crude oils, have been found to vary within a factor of 2. If a wrong value of $\lambda$ is used, the relaxation model will not fit the data. A poor fit manifests itself in the normalized goodness-of-fit parameter, $X^2$, being much greater than 1. Thus, a correct value of $\lambda$ for a particular fluid may be found by searching for the value that gives the minimum $X^2$. For North Sea crude oil, it was found that the parameter $\lambda = 0.51 \times 10^{-5}$ cm$^2$/s$^2$.

The parameter $\xi_o$ in Eq. 7 is the $T_1/T_2$ ratio of the crude oil. It has been established, for Larmor frequencies of a few MHz or less, that $\xi_o \approx 1$ for many crude oils with low-to-medium viscosities. The $T_1/T_2$ ratios of crude oils can be greater than 1 for high-viscosity oils and at higher Larmor frequencies because of the breakdown of the fast-motion condition.

The 3D distribution function for the brine phase can be written in the form, $$P_w(D,T_1,T_2) = P_w(T_2) \, \delta(D - D_w(T)) \, \delta(T_1 - \xi_w T_2)$$

(8) where $D_w(T)$ is the temperature-dependent molecular diffusion coefficient of water and $\xi_w$ is the apparent $T_1/T_2$ ratio of the water phase in the rock.

Substituting Eqs. 7 and 8 into Eq. 3 and using the properties of the Dirac delta functions to perform the integrations over D and $T_1$, one finds that the MRF relaxation model for DE sequences can be written as the sum of contributions from the water and oil phases; e.g., $$M(t, t_{e,l}) \approx \int dT_2 P_w(T_2) \exp\left(-\frac{t}{T_2}\right) I(t, t_{e,l}, D_w) f(W, \xi_w T_2) + \int dT_2 P_o(T_2) \exp\left(-\frac{t}{T_2}\right) I(t, t_{e,l}, \lambda T_2) f(W, \xi_o T_2) \quad (9)$$

The relaxation model in Eq. 9 is suitable for inverting suites of DE data. The details of the inversion follow along the lines previously given in the Freedman patent for suites of CPMG data. The inversion provides individual estimates of the water and crude oil $T_2$ distributions, $P_w(T_2)$ and $P_o(T_2)$.

The above described inversion method may be applied to NMR measurements obtained from fluids in the reservoir rocks using a logging tool or from formation fluids withdrawn into a formation fluid tester tool. Once the NMR relaxation time distributions from the reservoir rocks and from withdrawn fluid samples are derived, they can be compared to infer reservoir wettability. In order for this comparison to be meaningful, it is desirable that both suites of NMR measurements (reservoir rock measurements and formation fluid sample measurement) are made under substantially identical conditions, i.e., at substantially same temperature and pressure.

While the MRF method is used as an example in the above description of how to derive NMR parameters for individual constituents in a mixture, one skilled in the art will appreciate that other similar methods may be used without departing from the scope of the invention. For example, in situations where uncontaminated hydrocarbon samples are available, NMR relaxation time distributions may be estimated without applying the MRF method.

FIG. 6 summarizes steps involved in one method for evaluating reservoir wettability according to embodiments of the invention. First, a suite of downhole NMR data are collected from fluid samples in the reservoir rock in the formations at a selected axial depth (process 41). This may be performed with any suitable NMR logging tool, whether a wireline NMR tool or an MWD tool. As stated above, the suite of NMR data should include diffusion information in order to take advantage of the MRF method. To obtain NMR data including diffusion information, it is preferred that the above-described DE sequences be used. However, these data may also be obtained using the conventional CPMG pulse sequences. Data from DE pulse sequences may be acquired with an NMR well logging tool that has a programmable pulse sequence editor, such as the one described in U.S. Pat. No. 6,400,147 assigned to Schlumberger Technology Corporation. Once the suite of NMR data are available, they are inverted to give relaxation time ($T_1$, $T_2$ or $T_1/T_2$) distributions for individual components in the formation fluids (process 42). The inversion may use the MRF method.

Next, a suite of NMR data including diffusion information are obtained (process 44) using formation fluid samples extracted from the reservoir rocks at substantially the same axial depth (process 43). Extraction of formation fluid samples (process 43) may be accomplished with any suitable formation fluid testing tool, such as the Modular Formation Dynamics Tester (MDT™ from Schlumberger Technology, Houston, Tex.). The NMR measurements (process 44) may be performed with an NMR module that is part of the formation fluid testing tool. Alternatively, the NMR measurements may be performed in a laboratory, rather than downhole, using any suitable NMR instrument. In this case, the formation fluid samples will be transported from the formation fluid testing tool to the earth surface for analysis. Whether the NMR measurement is performed downhole or on the surface, it is preferred that the formation fluid samples be kept at substantially the same conditions (i.e., temperature and pressure) as they are in reservoir rocks in the formations. If the formation fluid samples are not kept at substantially the same conditions as they are in the reservoir rocks, the results will be less reliable because any dissolved gas or volatile component might be lost and the compositions of the fluids will be different. Again, the NMR measurements may involve using conventional CPMG pulse sequences or the new DE pulse sequences.

Once the suite of NMR data including diffusion information are available from the formation fluid sample, they are similarly inverted to produce relaxation time ($T_1$, $T_2$, or $T_1/T_2$) distributions of individual components in the fluids (process 45). The inversion may involve using the MRF method.

Next, the relaxation time ($T_1$, $T_2$ or $T_1/T_2$) distributions (process 42) from the first suite of NMR data obtained from reservoir rocks are compared (process 45) with the same relaxation time distributions (process 44) from the second suite of NMR data obtained from formation fluid samples. For example, if the crude oil $T_2$ distribution in the reservoir rock is shorter than the $T_2$ distribution in the formation fluid sample, then it can be inferred that the reservoir is oil-wet or mixed-wet. On the other hand, if the crude oil $T_2$ distribution in the reservoir rock is substantially the same as the $T_2$ distribution in the formation fluid sample, then the reservoir rock is water-wet. The comparison may be by comparing the center or the peak of each relaxation time distribution. The center as used herein refers to the center of mass of the relaxation times, while the peak means the highest point of the distribution curve. In addition to the center and the peak, the comparison may also be performed with the logarithmic means of the two relaxation time distributions. Alternatively, the two distribution curves may be normalized and then one curve (say, curve A) is subtracted from the other (say, curve B) to produce a difference curve (say, curve C). If difference curve C has positive values in the short $T_1$ or $T_2$ region and negative values in the long $T_1$ or $T_2$ region, then the relaxation time distribution in curve B has more shorter relaxation time components, and vice versa. Thus, the trend or distribution of positive and negative values in the difference curve may serve as a convenient indicator of how the $T_1$ or $T_2$ distributions have shifted.

Figure 7:
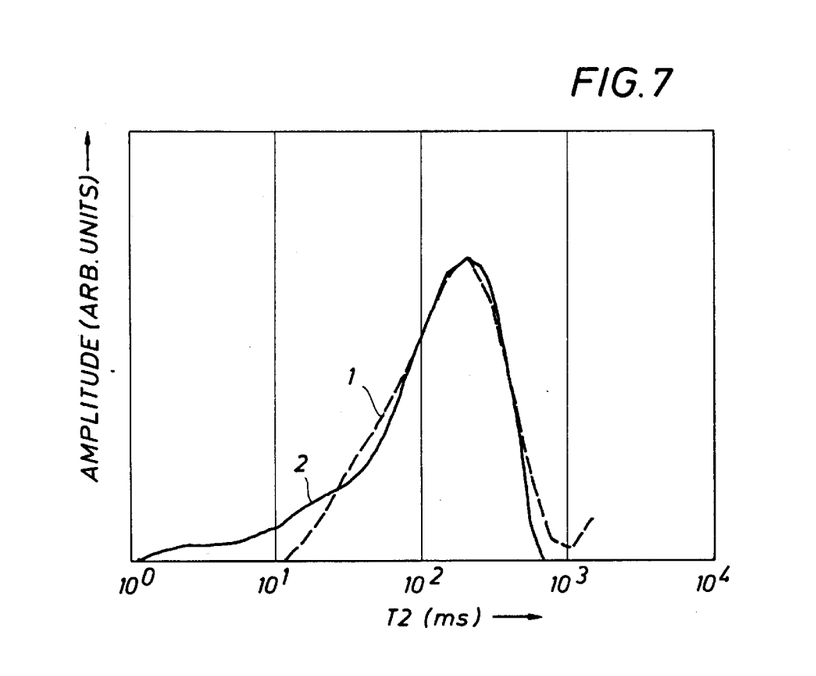
FIG. 7 shows an MRF-derived $T_2$ distribution from downhole NMR measurements as compared to a $T_2$ distribution of bulk oil measured in a laboratory.
Figure 8:
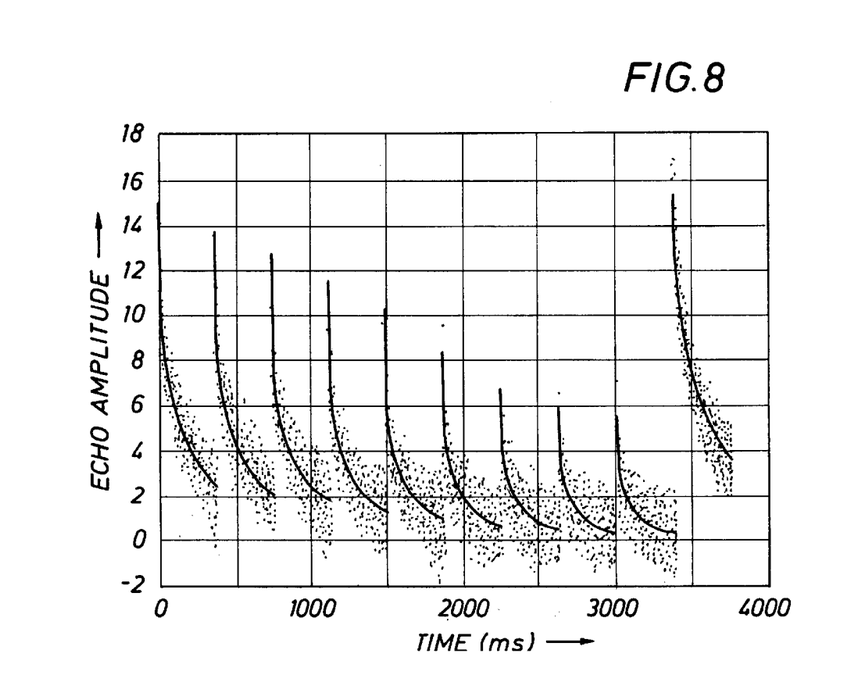
FIG. 8 shows the MRF fit to a suite of 10 NMR measurements obtained with DE pulse sequences.

The utility of the present invention will now be illustrated with the following examples. FIG. 7 shows a $T_2$ distribution crude oil computed by the MRF method (curve 1) from a suite of DE data acquired in a shallow sandstone formation containing medium viscosity oil (i.e., 16 cP under reservoir conditions). Also shown is the bulk oil $T_2$ distribution (curve 2) measured in the laboratory. The bulk oil is from a stock tank sample of produced reservoir oil. The bulk oil sample was heated and measured at reservoir temperature and pressure so that its $T_2$ distribution could be compared with that of the oil measured downhole. The downhole tool measurements used for the analysis in FIG. 7 were made using a suite of 10 diffusion-editing measurements. These data were inverted using the MRF method to compute the oil $T_2$ distribution in the rock. FIG. 8 shows the data suite and the MRF post-inversion fits to the data suite. The solid curves are the post-inversion fit of these data to the MRF relaxation model.

As shown in FIG. 7, the centers of the two oil $T_2$ distributions coincide and, hence, from these NMR measurements, the sandstone reservoir is predicted to be water-wet. In this particular case, the reservoir oil is a dead oil (i.e., it does not contain dissolved gases) and therefore its composition is similar to the stock tank oil. In general, the use of a stock tank sample for the measurement of the bulk oil $T_2$ distribution is not a good practice. The stock tank oil will be missing dissolved gases and possibly other volatile components and will not, in general, be representative of the reservoir oil. For this reason, the bulk oil measurement is preferably performed under the reservoir conditions (i.e., substantially the same pressure and temperature) on fluid samples using a downhole NMR fluid module.

Figure 9:
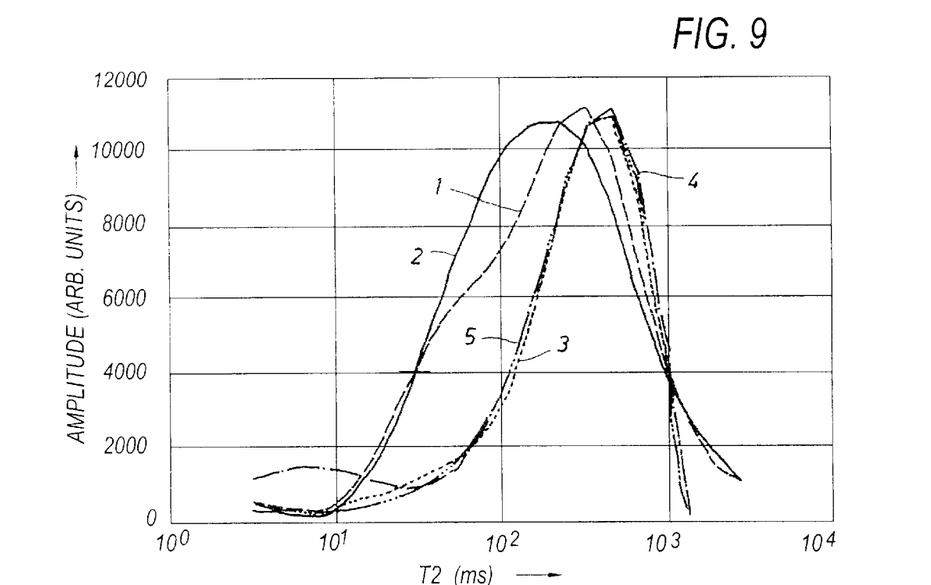
FIG. 9 shows crude oil $T_2$ distributions of four reservoir rock samples as derived with a method according to the invention and compared with a $T_2$ distribution of bulk oil.
Figure 10:
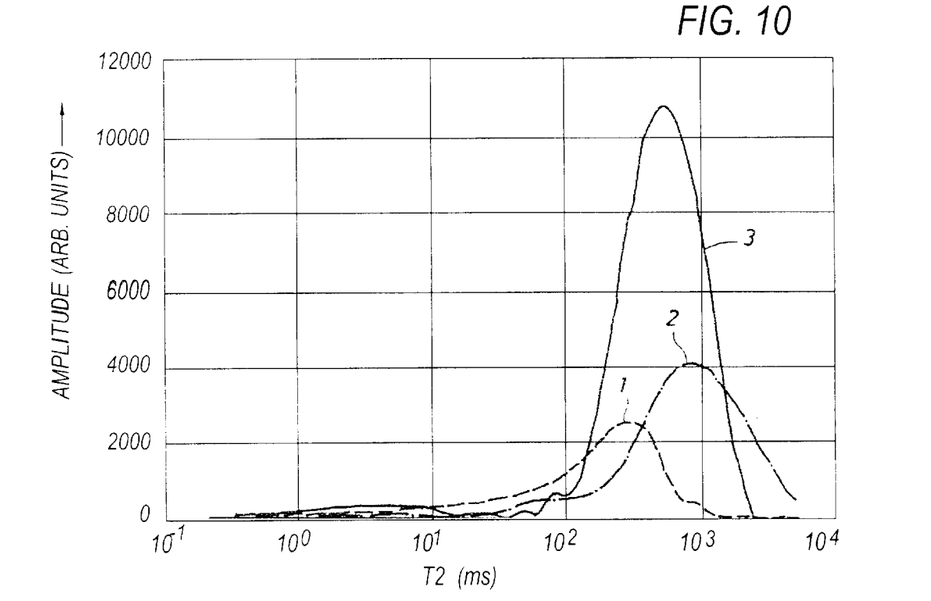
FIG. 10 shows brine $T_2$ distributions of two reservoir rock samples as derived with a method according to the invention and compared with a brine $T_2$ distribution of a 100% water saturated rock.

FIGS. 9 and 10 show the MRF computed oil and brine $T_2$ distributions, respectively, for core samples at various state of oil saturation. All core samples are in the shape of 1-inch-long cylinders with 1-inch diameter. These samples are wrapped in heat-shrinkable Teflon, brine saturated by vacuum, and then pressurized to remove any air. They are then submerged in the North Sea crude oil and centrifuged at 3400 rpm for 11 hours. The samples are then inverted and centrifuged for an additional hour. The samples at this stage are at high oil saturation and are referred to as the "drainage" ("DR") state. These samples are then submerged in brine for 16 hours to produce low oil saturation state, which will be labeled "imbibition" ("IM") state.

In FIG. 9, the MRF derived $T_2$ distributions are shown for four core samples at the IM state (curve 1–4): two Yates rocks (Y1312(IM) and Y1537(IM)), a Bentheim rock (BEN3(IM)), and a Berea rock (BER2(IM)). The bulk oil $T_2$ distribution (curve 5) is also shown in FIG. 9. The fact that the Yates samples, Y1312(IM) (curve 1) and Y1537(IM) (curve 2), are mixed-wet is obvious from the large shifts of their centers of $T_2$ distribution curves towards shorter $T_2$s relative to that of the bulk oil distribution (curve 5). It is equally clear that the two sandstone samples, BEN3(IM) (curve 3) and BER2(IM) (curve 4), are water-wet because their centers of $T_2$ distribution curves coincide with that of the bulk oil (curve 5).

To further corroborate that the Yates samples Y1312(IM) is mixed-wet, the brine $T_2$ distributions in the rocks are computed using the MRF method. In mixed or oil-wet rocks, it is expected that water molecules will relax more slowly than in the same rock containing 100% brine. This lengthening of $T_2$ relaxation times, relative to that of a 100% brine-wet rock, is observed as a shift of the center of brine $T_2$ distribution towards longer $T_2$ values. The MRF computed brine $T_2$ distribution of this rock at IM state is compared to those of the same rock at the DR state and the 100% saturated state. FIG. 10 shows that the centers of the MRF computed brine $T_2$ distributions for Y1312(IM) (curve 2) is indeed shifted to longer $T_2$ as compared to that for Y1312 (curve 3), which is 100% brine saturated. This is expected behavior for water in a mixed-wet rock and is consistent with the oil $T_2$ distribution for the same rock Y1312(IM) (curve 1 in FIG. 9).

FIG. 10 also shows that the same rock in the DR state (Y1312(DR), curve 1), which only has residual water in small pores, has a brine $T_2$ distribution shifted to shorter $T_2$ as compared to that of the 100% brine saturated state (YM1312, curve 3). This behavior is also expected because with residual water in small pores, most water molecules in Y1312(DR) are affected by surface relaxation. In contrast, some water molecules in the 100% water saturated state in the same rock are in large pores, and significant portion of the water molecules in the large pores are outside the range of influence of the paramagnetic ions on the rock surfaces. Accordingly, the brine $T_2$ distribution of Y1312(DR) is shifted to shorter $T_2$ as compared to that of the 100% water saturated state.

The advantages of the invention include the ability to determine reservoir rock wettability under downhole conditions. The ability to quickly and reliable determine reservoir rock wettability makes it possible for field engineers to decide a proper method for producing crude oils from the formations. The methods according to the invention may be practiced using existing tools. The methods take advantage of the robust MRF method and the new DE pulse sequences. The combination of the MRF method and the DE sequences makes it possible to easily derive $T_1$ or $T_2$ distributions for each component in the formation fluids; this will result in a significant saving of processing time.

While the invention has been described using limited examples, those skilled in the art, having the benefit of this disclosure, will appreciate that other methods can be devised without departing from the scope of the invention as disclosed herein. Accordingly, the scope of the invention should be limited only by the attached claims.

What is claimed is:

1. A method for determining downhole reservoir wettability, comprising:
    acquiring a first set of nuclear magnetic resonance measurements of formation fluids in earth formations at a selected axial depth along a borehole;
    inverting the first set of the nuclear magnetic resonance measurements to produce a first distribution of a spin relaxation parameter for a fluid component in the formation fluids;
    acquiring a second set of nuclear magnetic resonance measurements of a formation fluid sample removed by a formation fluid testing tool at the selected axial depth, the formation fluid sample being kept at a substantially same pressure and a substantially same temperature as those of the formation fluids in the earth formations at the selected axial depth;
    inverting the second set of nuclear magnetic resonance measurements to produce a second distribution of the spin relaxation parameter for the fluid component in the formation fluid sample;
    determining the reservoir wettability from a comparison of the first distribution of the spin relaxation parameter and the second distribution of the spin relaxation parameter.

2. The method of claim 1, wherein the acquiring the first set of nuclear magnetic resonance measurements and the acquiring the second set of nuclear magnetic resonance measurements are performed with a spin-echo pulse sequence.

3. The method of claim 2, wherein the spin-echo pulse sequence comprises a Carr-Purcell-Meiboom-Gill pulse sequence.

4. The method of claim 2 wherein the spin-echo pulse sequence comprises a diffusion-editing pulse sequence.

5. The method of claim 1, wherein the acquiring the first set of nuclear magnetic resonance measurements is performed with a wireline tool or a measurement-while-drilling tool.

6. The method of claim 1, wherein the acquiring the second set of nuclear magnetic resonance measurements is performed with a nuclear magnetic resonance module in a formation fluid testing tool at the selected axial depth.

7. The method of claim 1, wherein the acquiring the second set of nuclear magnetic resonance measurements is performed with a nuclear magnetic resonance instrument after the formation fluid sample is transferred to earth surface.

8. The method of claim 1, wherein the inverting the first set of the nuclear magnetic resonance measurements and the inverting the second set of the nuclear magnetic resonance measurements are performed with a magnetic resonance fluid characterization method.

9. The method of claim 1, wherein the spin relaxation parameter is one selected from the group consisting of a longitudinal relaxation time, a transverse relaxation time, and a ratio of the longitudinal and transverse relaxation time.

10. The method of claim 1, wherein the fluid component is a crude oil or brine.

11. The method of claim 1, wherein the comparison is based on centers of the first and the second distributions.

12. The method of claim 1, wherein the comparison is based on logarithmic means of the first and the second distributions.

13. The method of claim 1, wherein the comparison is based on peaks of the first and the second distributions.

14. The method of claim 1, wherein the comparison is performed based on a difference curve between the first and the second distributions.

* * * * *